United States Patent [19]

Valdes et al.

[11] Patent Number: 4,761,277

[45] Date of Patent: Aug. 2, 1988

[54] WATERBASE LIPLINER FORMULATION

[75] Inventors: Nancy E. Valdes, Ramsey; Gary Linstra, Jr., Point Pleasant; Ann M. Krog, Red Bank, all of N.J.

[73] Assignee: Charles of the Ritz Group Ltd., New York, N.Y.

[21] Appl. No.: 946,991

[22] Filed: Dec. 29, 1986

[51] Int. Cl.$^4$ .................... A61K 31/79; A61K 7/025
[52] U.S. Cl. ........................ 424/64; 424/80; 424/401
[58] Field of Search ............ 424/64, 80, 401

[56] References Cited

U.S. PATENT DOCUMENTS

| | | | |
|---|---|---|---|
| 2,230,063 | 1/1941 | Klimist | 424/64 |
| 3,953,591 | 4/1976 | Snyder | 424/80 |
| 4,120,949 | 9/1978 | Bapatla et al. | 424/80 |

FOREIGN PATENT DOCUMENTS

| | | | |
|---|---|---|---|
| 519913 | 4/1972 | Switzerland | 424/64 |

*Primary Examiner*—Ronald W. Griffin
*Assistant Examiner*—Nancy S. Carson
*Attorney, Agent, or Firm*—Lerner, David, Littenberg, Krumholz & Mentlik

[57] ABSTRACT

A waterbase lipliner composition in the form of a liquid is provided which is especially adapted for use in conjunction with a wick-type nib pen which delivers lipliner through a capillary action, which lipliner composition includes a water-soluble organic pigment formed of FDA approved organic pigments, a water-soluble organic polymer film-former, which is a mixture of polyvinyl pyrrolidone and polyvinyl alcohol, and optionally one or more plasticizers, preservatives, moisturizers and/or humectants, and water as a carrier for the pigment. The lipliner composition of the invention has a viscosity of less than 750 cps and will pass through the wick of a wick-type nib pen by capillary action without clogging the wick.

16 Claims, No Drawings

WATERBASE LIPLINER FORMULATION

FIELD OF THE INVENTION

The present invention relates to an improved water-resistant waterbase lipliner composition which is especially adapted for delivery by a wick-type nib pen and includes FDA approved water-soluble organic pigments.

BACKGROUND OF THE INVENTION

A wick-type nib pen which delivers a steady flow of coloring liquid has been available in Europe and Japan as a delivery system for eyeliner cosmetics. The nib pen is similar in construction to cartridge-type pens and includes a shell portion having a wick formed of acrylic fiber of desired porosity extending out from one end, and covered with polyurethane foam and which shell is adapted to hold a liquid eyeliner cartridge. The liquid eyeliner flows from the cartridge into the wick and is subsequently delivered by capillary action to the user.

Until now, nib pens have not been employed as a delivery system for lipliner because conventional lipliner compositions employ wax or anhydrous (oil) base which are relatively viscous (viscosity of greater than 1000 cps) and would therefore cause clogging of the wick. Furthermore, it has been found that such prior art lipliners do not hold the lipline when lipstick has been applied because the wax or anhydrous base lipliners mix with the users oil sweat causing solubilizing of the lipliner.

Accordingly, a need exists in the U.S. for a lipliner composition which may be employed with a wick-type nib pen without causing clogging.

BRIEF STATEMENT OF THE INVENTION

In accordance with the present invention, an improved water-resistant lipliner composition is provided which may be delivered by wicking action from a nib pen and which is formed of one or more FDA approved water-soluble organic pigments, a water-soluble polymer film-forming agent, which includes a combination of polyvinyl pyrrolidone and polyvinyl alcohol, water as a carrier, optionally one or more plasticizers, optionally one or more preservatives, and optionally one or more moisturizers and/or optionally one or more humectants. The complete lipliner formulation of the invention will have a viscosity of less than about 750 cps, and preferably less than about 500 cps to ensure that it will not cause clogging when used in a nib pen.

DETAILED DESCRIPTION OF THE INVENTION

The lipliner composition of the invention will contain FDA approved water-soluble organic pigments in an amount within the range of from 0 to about 10% and preferably from about 0.1 to about 5% by weight of the total lipliner composition. Examples of such water-soluble organic pigments include, but are not limited to, D&C Red 33, FD&C Yellow 6, FD&C Yellow 5, FD&C Blue 1 and other organic water-soluble FD&C and D&C approved colors or pigments.

The water-soluble aqueous polymer film-forming agent will preferably comprise a combination of polyvinyl pyrrolidone and polyvinyl alcohol. Polyvinyl pyrrolidone is available under the tradenames PVP, PVP-K30, Plasdone, Polycar AT, Peregal SKT, Kollidon and Albigen A. The above film-forming agent (that is, polyvinyl pyrrolidone) will be employed in the lipliner formulation in amounts within the range of from about 2.5 to about 25% and preferably from about 5 to about 15% by weight of the total lipliner formulation.

The polyvinyl alcohol component is available commercially as Covol (CPC International), Elvanol (DuPont) and Gelvatol (Monsanto) and will be employed in amounts within the range of from about 0.5 to about 10% by weight and preferably from about 1 to about 5% by weight of the total lipliner formulation.

The combination of the above film-forming agents will include polyvinyl pyrrolidone in a weight ratio to polyvinyl alcohol of within the range of from about 0.25:1 to about 50:1 and preferably from about 1:1 to about 15:1.

In addition, the lipliner composition of the invention will optionally include a plasticizer for the film-forming agent which may include polysorbate 20, propylene glycol, carboxymethyl cellulose, cellulose acetate, cellulose acetate propionate, dibutyl tartrate, diethylene glycol, dimethylene phthalate, glycerine, shellac, sorbitol or oleyl alcohol with polysorbate 20 being preferred. Polysorbate 20 is a mixture of laurate esters of sorbitol or sorbitol anhydrides, formed predominantly of the mono ester and condensed with approximately 20 moles of ethylene oxide, with propylene glycol, polysorbate 20, glycerine or mixtures thereof being preferred. The plasticizer for the film forming agent will be employed in an amount within the range of from about 1 to about 15% and preferably from about 3 to about 10% by weight of the lipliner formulation.

Water will be present as the carrier for the water-soluble organic pigments in an amount within the range of from about 45 to about 90% and preferably from about 60 to about 85% by weight based on the total weight of the lipliner formulation to ensure that all pigments are fully dissolved.

A preservative may also be present in the lipliner formulation, such as phenoxy ethanol, ethyl paraben, butyl paraben, methyl paraben, propyl paraben, imidazolinyl urea, dimethyldimethoyl hydantoin, N-(3-chloroallyl)hexaminium chloride, cetrimonium bromide, trisodium ethylene diamine tetraacetic acid and/or butylated hydroxy anisole with a mixture of phenoxy ethanol and one or more parabens being preferred. The preservative will be present in an amount within the range of from about 0.1 to about 3% and preferably from about 0.5 about 1.5% by weight of the total lipliner formulation.

Various other conventional ingredients which may optionally be present in the carrier include one or more moisturizers, such as L-pyroglutamatic acid, sodium pyroglutamate, hydrolyzed animal collagen, hydrolyzed animal protein, with sodium L-pyroglutamate being preferred, in an amount within the range of from 0 to about 0.5% and preferably from about 0.02 to about 0.2% by weight of the total lipliner formulation.

Preferred lipliner compositions of the invention are set out below.

| Ingredient | Parts by Weight |
| --- | --- |
| Polyvinyl pyrrolidone | 5 to 15 |
| Polyvinyl alcohol | 1 to 5 |
| Water-soluble organic pigments | 0 to 5 |
| Deionized water | 60 to 85 |
| Propylene glycol | 1 to 10 |

-continued

| | |
|---|---|
| Polysorbate 20 | 0.5 to 3 |
| Na-pyroglutamate acid | 0.02 to 20 |
| Glycerin | 0.1 to 5 |
| Preservative (preferably Phenonip*) | 0.5 to 1.5 |
| (Viscosity) | less than 300 cps |

| *Phenonip | Parts by Weight per 100 parts preservative |
|---|---|
| Phenoxy ethanol | 72 |
| Ethylparaben | 4 |
| Butylparaben | 6 |
| Methylparaben | 16 |
| Propylparaben | 2 |

The above lipliner composition is especially suited for use with a cartridge type nib pen in that the pigments present therein will be completely solubilized in the water and will therefore pass through the wick of the nib pen by capillary action without causing clogging.

In forming the lipliner of the invention, the polyvinyl alcohol is dissolved in water with propeller mixing and heated at a temperature within the range of from about 70° to about 80° C. The solution is removed from the heat and the polyvinyl pyrrolidone is added and mixed until dissolved. The organic pigments are mixed into the solution until the pigments are dissolved. The mix is cooled to from about 45° to about 50° C. Thereafter, the plasticizers, moisturizers, if present, and preservatives are added with mixing. Mixing is continued until a uniform mixture is obtained. The so-formed mix may then be inserted into a cartridge which may be fed into a nib-type pen equipped with a wick.

The following Example represents a preferred embodiment of the present invention.

EXAMPLE

A lipliner composition containing FDA approved water-soluble organic pigments that can be applied by a nib pen having the following composition was prepared as described below.

| | | % W/W |
|---|---|---|
| Phase A | | |
| Deionized water | | 80.5 |
| Polyvinyl pyrrolidone | (film former) | 7.5 |
| Polyvinyl alcohol | | 2.0 |
| Phase B | | |
| Water-soluble organic pigments - D & C Red 33 | | 3.0 |
| Phase C | | |
| Propylene glycol | ⎫ | 3 |
| | ⎬ moisturizer | |
| Polysorbate 20 | ⎭ | 1 |
| Adjidew solution* | | 2 |
| Phenonip** (preservative) | | 1 |
| *Adjidew solution | | |
| Propylene glycol | | 75 |
| Glycerine | | 20 |
| Sodium pyroglutamate | | 5 |

| **Phenonip | % by Weight of Preservative Present |
|---|---|
| Phenoxy ethanol | .36 |
| Ethyl paraben | .02 |
| Butyl paraben | .03 |
| Methyl paraben | .08 |
| Propyl paraben | .01 |

Phase A ingredients were added to a suitable vessel and heated with propeller mixing for 30 minutes to 70° C. to form a solution. Heating was removed and pigment was added with a propeller mixing for about 10 minutes until the pigment was dissolved. The so-formed solution was cooled to 50° C. and Phase C was added and mixing was continued for 15 minutes until a uniform liquid lipliner composition was obtained.

The resulting liquid lipliner composition had a viscosity of less than about 300 cps and was found to be suitable for use in a wick-type nib lipliner pen and was delivered by capillary action without clogging the wick and pen. In addition, the so-formed lipliner when applied kept its lipline, even after lipstick was applied, for several hours. The so-formed lipliner also had improved water-resistance over similar lipliner compositions containing 15% by weight polyvinyl pyrrolidone and no polyvinyl alcohol.

What is claimed is:

1. A water resistant lipliner composition in the form of a flowable liquid dispersion or solution comprising one or more water-soluble organic pigments, water as a carrier therefor, and a water-soluble organic polymer film-forming agent which is a combination consisting essentially of polyvinyl pyrrolidone and polyvinyl alcohol, said composition having a viscosity of less than about 750 cps.

2. The composition as defined in claim 1 wherein said polyvinyl pyrrolidone is employed in a weight ratio to polyvinyl alcohol of within the range of from about 0.25:1 to about 50:1.

3. The composition as defined in claim 1 wherein said organic pigment comprises D&C Red 33, FD&C Yellow 6, FD&C Yellow 5, FD&C Blue 1 or mixtures thereof.

4. The composition as defined in claim 1 wherein said organic pigment comprises from 0.1% to about 10% by weight of said composition and said water comprises from about 45 to about 90% by weight of said composition.

5. The composition as defined in claim 1 wherein said polyvinyl pyrrolidone comprises from about 2.5 to about 25% by weight, and said polyvinyl alcohol comprises from about 0.5 to about 10% by weight, said % being based on the total weight of said composition.

6. The composition as defined in claim 5 wherein said polyvinyl pyrrolidone comprises from about 5 to about 15% by weight and said polyvinyl alcohol comprises from about 1 to about 5% by weight.

7. The composition as defined in claim 1 further comprising a plasticizer which is polysorbate 20, propylene glycol or mixtures thereof, a preservative which is a mixture of phenoxy ethanol, ethyl paraben, butyl paraben, methyl paraben and propyl paraben, and and a moisturizer which is sodium pyroglutamate and a humectant which is glycerine and said composition has a viscosity of less than 300 cps.

8. The composition as defined in claim 1 further including a plasticizer.

9. The composition as defined in claim 8 wherein said plasticizer is polysorbate 20, propylene glycol, glycerine or mixtures thereof.

10. The composition as defined in claim 9 wherein said plasticizer is present in an amount within the range of from about 1 to about 15% by weight of said lipliner composition.

11. The composition as defined in claim 8 comprising from about 0.1 to about 5% by weight organic pigment, from about 5 to about 15% by weight polyvinyl pyrrolidone film forming agent, from about 1 to about 5% by weight polyvinyl alcohol, from about 60 to about 85% by weight water, and from about 1 to about 10% by weight plasticizer, said % being based on the total weight of said composition, said composition having a viscosity of less than 500 cps.

12. The composition according to claim 8 further comprising a preservative.

13. The composition as defined in claim 12 comprising from about 60 to about 85% by weight water, from about 1 to about 10% by weight plasticizer, and from about 0.5 to about 1.5% by weight preservative, said % being based on the total weight of said composition.

14. The composition as defined in claim 13 wherein said plasticizer is propylene glycol, polysorbate 20, glycerine or mixtures thereof, and said preservative is phenoxyethanol, one or more alkyl parabens or mixtures thereof.

15. The composition according to claim 1 further comprising a moisturizer.

16. The composition as defined in claim 15 further including a moisturizer comprising sodium pyroglutamate and a humectant comprising glycerine.

* * * * *

UNITED STATES PATENT AND TRADEMARK OFFICE
CERTIFICATE OF CORRECTION

PATENT NO. : 4,761,277

DATED : August 2, 1988

INVENTOR(S) : Valdes et al.

It is certified that error appears in the above-identified patent and that said Letters Patent is hereby corrected as shown below:

Column 2, line 53, "L-pyroglumtamatic" should read --L-pyroglutamic--.
Column 4, line 51, cancel the second "and".

Signed and Sealed this

Fourteenth Day of March, 1989

Attest:

DONALD J. QUIGG

*Attesting Officer*      *Commissioner of Patents and Trademarks*